US009922417B2

(12) United States Patent
Sela et al.

(10) Patent No.: US 9,922,417 B2
(45) Date of Patent: Mar. 20, 2018

(54) SYSTEM AND METHOD FOR DETECTING TISSUE AND FIBER TRACT DEFORMATION

(71) Applicants: Gal Sela, Toronto (CA); Simon Alexander, Toronto (CA); Cameron Piron, Toronto (CA); Joshua Richmond, Toronto (CA); Michael Wood, Toronto (CA); Murugathas Yuwaraj, Markham (CA); David Gallop, Toronto (CA); Wes Hodges, London (CA); Monroe M. Thomas, Toronto (CA)

(72) Inventors: Gal Sela, Toronto (CA); Simon Alexander, Toronto (CA); Cameron Piron, Toronto (CA); Joshua Richmond, Toronto (CA); Michael Wood, Toronto (CA); Murugathas Yuwaraj, Markham (CA); David Gallop, Toronto (CA); Wes Hodges, London (CA); Monroe M. Thomas, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

(21) Appl. No.: 14/769,507

(22) PCT Filed: Mar. 14, 2014

(86) PCT No.: PCT/CA2014/050243
§ 371 (c)(1),
(2) Date: Aug. 21, 2015

(87) PCT Pub. No.: WO2014/138997
PCT Pub. Date: Sep. 18, 2014

(65) Prior Publication Data
US 2016/0005169 A1    Jan. 7, 2016

Related U.S. Application Data

(60) Provisional application No. 61/799,921, filed on Mar. 15, 2013, provisional application No. 61/800,787, (Continued)

(51) Int. Cl.
A61B 34/10 (2016.01)
A61B 90/11 (2016.01)
(Continued)

(52) U.S. Cl.
CPC .......... *G06T 7/0012* (2013.01); *A61B 5/0066* (2013.01); *A61B 34/10* (2016.02);
(Continued)

(58) Field of Classification Search
None
See application file for complete search history.

(56) References Cited

U.S. PATENT DOCUMENTS 6,246,895 B1 * 6/2001 Plewes .................... A61B 8/00
324/309
2004/0009459 A1    1/2004 Anderson
(Continued)

FOREIGN PATENT DOCUMENTS

CN         103462606 A2 * 12/2013 ............ A61B 5/055
DE      102011087357 A1    5/2013
(Continued)

OTHER PUBLICATIONS

Walter Stummer, Mechanisms of tumor-related brain edema, Neurosurg. Focus / vol. 22 / May.*
(Continued)

*Primary Examiner* — Sumati Lefkowitz
*Assistant Examiner* — Jiangeng Sun
(74) *Attorney, Agent, or Firm* — Hill & Schumacher

(57) ABSTRACT

Disclosed herein is a method for producing an evolvable tissue model of a patient and, using this model, modelling physical transformations of the tissue (e.g. deformation) of the tissue model by interacting the tissue model with influence models which model interactions with the tissue such as surgical instruments, pressure, swelling, temperature changes etc. The model is produced from a set of input data of the tissue which includes directional information of the tissue. The directional information is used to produce an oriented tissue map. A tissue model is then produced from the oriented tissue map such that the tissue model reflects the directionality of the tissue component. When the tissue model is subjected to an influence that causes tissue deformation over a period of time, the tissue model directionally deforms over the period of time in a manner which reflects a trajectory of the influence interacting with the directionality of the tissue component.

20 Claims, 9 Drawing Sheets

Related U.S. Application Data filed on Mar. 15, 2013, provisional application No. 61/800,155, filed on Mar. 15, 2013, provisional application No. 61/924,993, filed on Jan. 8, 2014.

(51) Int. Cl.
    *G06T 7/00*     (2017.01)
    *A61B 5/00*     (2006.01)
    *G09B 23/30*     (2006.01)
    *A61B 5/055*     (2006.01)

(52) U.S. Cl.
    CPC .............. *G09B 23/30* (2013.01); *A61B 5/055* (2013.01); *A61B 90/11* (2016.02); *A61B 2034/105* (2016.02); *G06T 2207/30012* (2013.01)

(56) References Cited

U.S. PATENT DOCUMENTS

| | | | |
|---|---|---|---|
| 2009/0198129 A1* | 8/2009 | Varghese | A61B 8/0858 600/438 |
| 2011/0196253 A1* | 8/2011 | McIntyre | A61N 1/36082 600/547 |
| 2012/0232386 A1 | 9/2012 | Mansi | |
| 2013/0047103 A1 | 2/2013 | Avisar | |
| 2013/0204287 A1 | 8/2013 | Mark et al. | |
| 2014/0171873 A1 | 6/2014 | Mark | |
| 2014/0294270 A1* | 10/2014 | Schneider | A61B 5/055 382/131 |
| 2015/0351722 A1* | 12/2015 | Chen | A61B 8/485 600/427 |

FOREIGN PATENT DOCUMENTS

| | | |
|---|---|---|
| EP | 1980201 A2 | 10/2008 |
| WO | 2007007303 | 1/2007 |
| WO | 2009099340 | 8/2009 |
| WO | 2012125829 A2 | 9/2012 |

OTHER PUBLICATIONS

International Search Report (PCT/CA 2014/050243) dated Jul. 15, 2014.
Written Opinion (PCT/CA2014/050243 ) dated Jul. 15, 2014.
Bucki et al. Bio-Mechanical Model of the Brain for a Per-Operative Image-Guided Neuronavigator Compensating for "Brian-Shift" Deformations.
West, JD et al.,"Incorporation of Diffusion Tensor Anisotropy in Brain Deformation Models for Updating Preoperative Images to Improve Image-Guidance", Biomedical Imaging, 2002. Proceedings. 2002 IEEE International Symposium on Biomedical Imaging, Jul. 7-10, 2002, pp. 509-512.
European Search Report from EP2967343 dated Feb. 3, 2017.

\* cited by examiner

SYSTEM AND METHOD FOR DETECTING TISSUE AND FIBER TRACT DEFORMATION

CROSS-REFERENCE TO RELATED APPLICATIONS

This application is a National Phase application claiming the benefit of the international PCT Patent Application No. PCT/CA2014/050243, filed on Mar. 14, 2014, in English, which claims priority to U.S. Provisional Application No. 61/799,921, titled "SYSTEM AND METHOD FOR DETECTING TISSUE AND FIBER TRACT DEFORMATION" and filed on Mar. 15, 2013, the entire contents of which are incorporated herein by reference.

This application claims priority to U.S. Provisional Application No. 61/800,787, titled "POLARIZED LIGHT IMAGING DEVICE" and filed on Mar. 15, 2013, the entire contents of which are incorporated herein by reference.

This application claims priority to U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013, the entire contents of which are incorporated herein by reference.

This application claims priority to U.S. Provisional Application No. 61/924,993, titled "PLANNING, NAVIGATION AND SIMULATION SYSTEMS AND METHODS FOR MINIMALLY INVASIVE THERAPY" and filed on Jan. 8, 2014, the entire contents of which are incorporated herein by reference.

FIELD

The present disclosure relates to navigation systems and methods for minimally invasive therapy and image guided medical procedures.

BACKGROUND

Surgical procedures which exert pressure on tissues and organs, or alter their composition, can tend to produce deformation of tissue. For example, deformation of brain tissue may occur when a craniotomy is opened and pressure on the brain is relieved, when a surgical device such as a surgical port or catheter is introduced into the brain, or when tissue is removed during surgery such as in a tumour resection. Deformation of tissue and its effects on the accuracy and precision of surgical procedures is an ongoing area of investigation and research, and there is a need for effective means to detect such deformation for surgical planning, navigation, and analysis. While much of the following discussion uses surgical procedures in the brain as examples, similar issues arise in surgery to the spine and other orthopedic applications and the techniques are generally applicable.

The complexities associated with tissue shifts that occur during surgery are not well addressed by currently available systems and methods. For example during a craniotomy, when a large portion of the skull of a patient is removed to allow for access to the brain, the brain tends to swell outside of the remaining skull that is encasing the brain due to a pressure differential between the brain and the operating room. This brain swelling, and brain sag due to gravity, can tend to lead to a significant shift in the brain tissue, often on the order of 1-2 cm. Additionally, as a tumor is resected from the brain the position of the remaining tissue tends to shift relative to the pre-operative images as a result of the decreased volume. These mechanisms of brain swelling, sag, and shift can result in significant variations between pre and intra operative brain position. There is therefore a need for effective means to detect tissue deformation resulting from various causes including tissue resection, swelling, and surgical tool insertions, to allow for improved surgical planning, navigation, and analysis.

Deformations of the brain tissues occur in the course of surgery because of physical and physiological phenomena. As a consequence of this brain-shift, images acquired pre-operatively no longer correspond to the positioning of brain tissue. For this reason, any preoperative based neuro-navigation planning is compromised by intraoperative brain deformations. According to Buick et al [Bio-Mechanical Model of the Brain for a Per-Operative Image-Guided Neuronavigator Compensating for "Brain-Shift" Deformations], mathematical computer simulation models such as continuous mechanical linear and small deformations model may be used to model surgical interactions (i.e., tissue resection) in an interactive way.

Different tissue types possess different deformation properties, so current methods of detecting tissue deformation often segment the body into a variety of tissue types. For example, with respect to deformation with brain surgery, brain tissue tends to be analyzed based on tissue type such as grey matter, white matter and cerebrospinal fluid. These methods provide deformation models based on the distortion properties for each type of tissue. However, these current methods do not adjust the model based on knowledge of oriented tissue structure (such as nerve or muscle fiber direction) or connectivity of the underlying structure. Rather, these systems and methods tend to treat all similar tissue types homogenously. Hence there is a need for a system and method of detecting tissue deformation based on knowledge of oriented tissue structure or connectivity of the underlying structure, rather than simply tissue type. Furthermore, if the device being introduced to the tissue is geometrically of similar shape and size to its ingress and sufficiently rigid, the device will tend to constrain movement of tissue and will maintain an interface with the tissue of known position and shape, and so is significant to the equilibrium positioning of tissue.

SUMMARY

There is herein described a system and method for detecting tissue generally transformation (such as tissue deformation), including nerve fiber deformation. The systems and methods described in this disclosure provide way to model and hence predict tissue transformations (e.g., tissue and fiber deformation), based on properties of the tissue orientation at a given location (for example, the local direction of each fiber tract at a given point), as well as knowledge of known events in the environment of the tissue (for example, edema or removal of surrounding tissue).

An embodiment provides a method for producing an evolvable tissue model of a patient, comprising the steps of:

a) receiving at least one set of input data of tissue of a patient, said at least one set of input data containing directional information being derivable therefrom, of at least one tissue component of the tissue;

b) representing the directional information of the at least one component of tissue in a pre-selected format and producing therefrom an oriented tissue map which reflects a directionality of the at least one tissue component; and c) producing a tissue model in which at least one constituent of the tissue model is the oriented tissue map such that the tissue model reflects the directionality of the at least one tissue component so that when the tissue model is subjected to an influence that causes tissue transformation over a period of time, the tissue model evolves over the period of time in a manner which reflects a trajectory of the influence interacting with the directionality of the at least one tissue component.

This tissue model may then be interacted with one or more influences to predict transformations of the tissue due to the influence. This involves receiving at least one set of input data of at least one influence to which the tissue is to be subjected;

preprocessing the at least one set of input data and extracting therefrom parameters of said influence;

representing the parameters of said influence in a pre-selected format; and producing at least one influence model from the represented parameters of the influence; and interacting the influence model with the tissue model and updating the tissue model after the interaction showing a transformation the tissue model due to the influence, the updated tissue model forming an output.

Also disclosed herein is a system for producing an evolvable tissue model of a patient, comprising:

a) a storage device configured to receive and store therein pre-operative and intra-operative input data of tissue of a patient;

b) a computer processor and associated user interface in communication with said storage device, said computer processor being programmed with instructions for:

receiving at least one set of input data of tissue of a patient, said at least one set of input data containing directional information being derivable therefrom, of at least one tissue component of the tissue;

representing the directional information of the at least one component of tissue in a pre-selected format and producing therefrom an oriented tissue map which reflects a directionality of the at least one tissue component; and producing a tissue model in which at least one constituent of the tissue model is the oriented tissue map such that the tissue model reflects the directionality of the at least one tissue component so that when the tissue model is subjected to an influence that causes tissue transformation over a period of time, the tissue model evolves over the period of time in a manner which reflects a trajectory of the influence interacting with the directionality of the at least one tissue component;

storing said tissue model; and c) a visual display for displaying the tissue model.

There is also disclosed a system for predicting or modelling a transformation of an evolvable tissue model of a patient due to interaction with an influence, a) a storage device;

b) a computer processor and associated user interface in communication with said storage device, said computer processor being programmed with instructions for:

receiving at least one set of input data of at least one influence to which the tissue is to be subjected;

preprocessing the at least one set of input data and extracting therefrom parameters of said influence;

representing the parameters of said influence in a pre-selected format; and producing at least one influence model from the represented parameters of the influence;

interacting the influence model with a tissue model and updating the tissue model after the interaction for showing a transformation the tissue model due to the influence; and c) a visual display for displaying any one or combination of the tissue model, the influence model and the transformed tissue model.

The present disclosure also provides a computer readable storage medium having stored therein a computer program for predicting a transformation of an evolvable tissue model of a patient due to interaction with an influence, the computer program being programmed with steps, which, when executed on a computer, comprises:

receiving at least one set of input data of at least one influence to which the tissue is to be subjected;

preprocessing the at least one set of input data and extracting therefrom parameters of said influence;

representing the parameters of said influence in a pre-selected format; and producing at least one influence model from the represented parameters of the influence;

interacting the influence model with a tissue model and updating the tissue model after the interaction for showing a transformation the tissue model due to the influence; and visually displaying the transformed tissue model.

A computer readable storage medium is also provided having stored therein a computer program for producing an evolvable tissue model of a patient and for predicting a transformation of an evolvable tissue model of a patient due to interaction with an influence, the computer program being programmed with steps, which, when executed on a computer, comprises:

receiving at least one set of input data of tissue of a patient, said at least one set of input data containing directional information being derivable therefrom, of at least one tissue component of the tissue;

representing the directional information of the at least one component of tissue in a pre-selected format and producing therefrom an oriented tissue map which reflects a directionality of the at least one tissue component;

producing a tissue model in which at least one constituent of the tissue model is the oriented tissue map such that the tissue model reflects the directionality of the at least one tissue component so that when the tissue model is subjected to an influence that causes tissue transformation over a period of time, the tissue model evolves over the period of time in a manner which reflects a trajectory of the influence interacting with the directionality of the at least one tissue component;

storing said tissue model;

receiving at least one set of input data of at least one influence to which the tissue is to be subjected;

preprocessing the at least one set of input data and extracting therefrom parameters of said influence;

representing the parameters of said influence in a pre-selected format; and producing at least one influence model from the represented parameters of the influence;

interacting the influence model with the tissue model and updating the tissue model after the interaction for showing a transformation the tissue model due to the influence; and visually displaying the transformed tissue model.

Furthermore, as the systems and methods described herein predict and model transformations such as deformation based on location and directional based properties of particular fiber tracts, they do not require a segmentation of tissue types for deformation estimation; however, in some embodiments this information can be utilized.

A further understanding of the functional and advantageous aspects of the present system and method can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Various apparatuses or processes will be described below to provide examples of embodiments of the invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention.

Furthermore, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Furthermore, in the following passages, different aspects of the embodiments are defined in more detail. Each aspect so defined may be combined with any other aspect or aspects unless clearly indicated to the contrary. In particular, any feature indicated as being preferred or advantageous may be combined with at least one other feature or features indicated as being preferred or advantageous.

Figure 1:
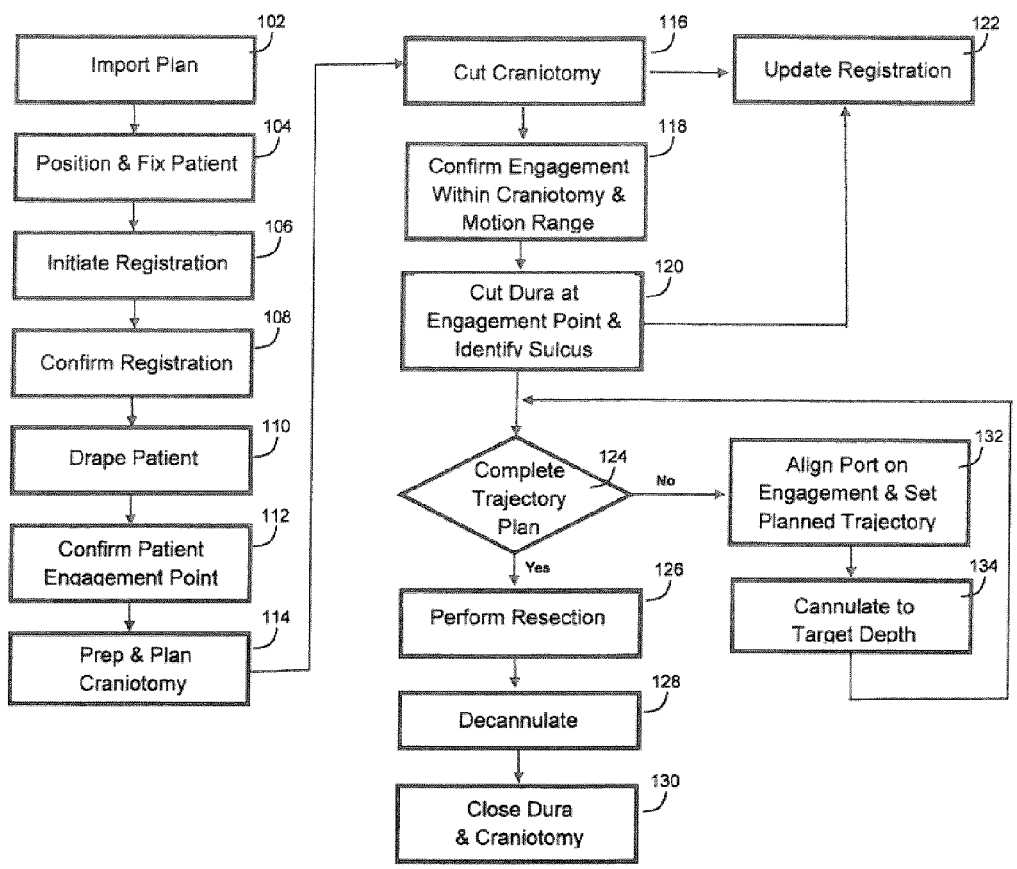
FIG. 1 is a flow chart illustrating the processing steps involved in a port-based surgical procedure using a navigation system.

FIG. 1 is a flow chart illustrating the processing steps involved in a port-based surgical procedure using a navigation system. The first step involves importing the port-based surgical plan (step 102). A detailed description of the process to create and select a surgical plan is outlined in the disclosure "PLANNING, NAVIGATION AND SIMULATION SYSTEMS AND METHODS FOR MINIMALLY INVASIVE THERAPY", a United States Patent Publication based on a United States Patent Application, which claims priority to U.S. Provisional Patent Application Ser. Nos. 61/800,155 and 61/924,993, which are both hereby incorporated by reference in their entirety.

As outlined above; an exemplary plan may be composed of pre-operative 3D imaging data (e.g., MRI, Ultrasound, etc.), and overlaid on it, received inputs (e.g., sulci entry points, target locations, surgical outcome criteria, additional 3D image data information) and displaying one or more trajectory paths based on the calculated score for a projected surgical path. The aforementioned surgical plan may be one example; other surgical plans and/or methods may also be envisioned and may form the planning input into the present guidance and navigation system.

Figure 2:
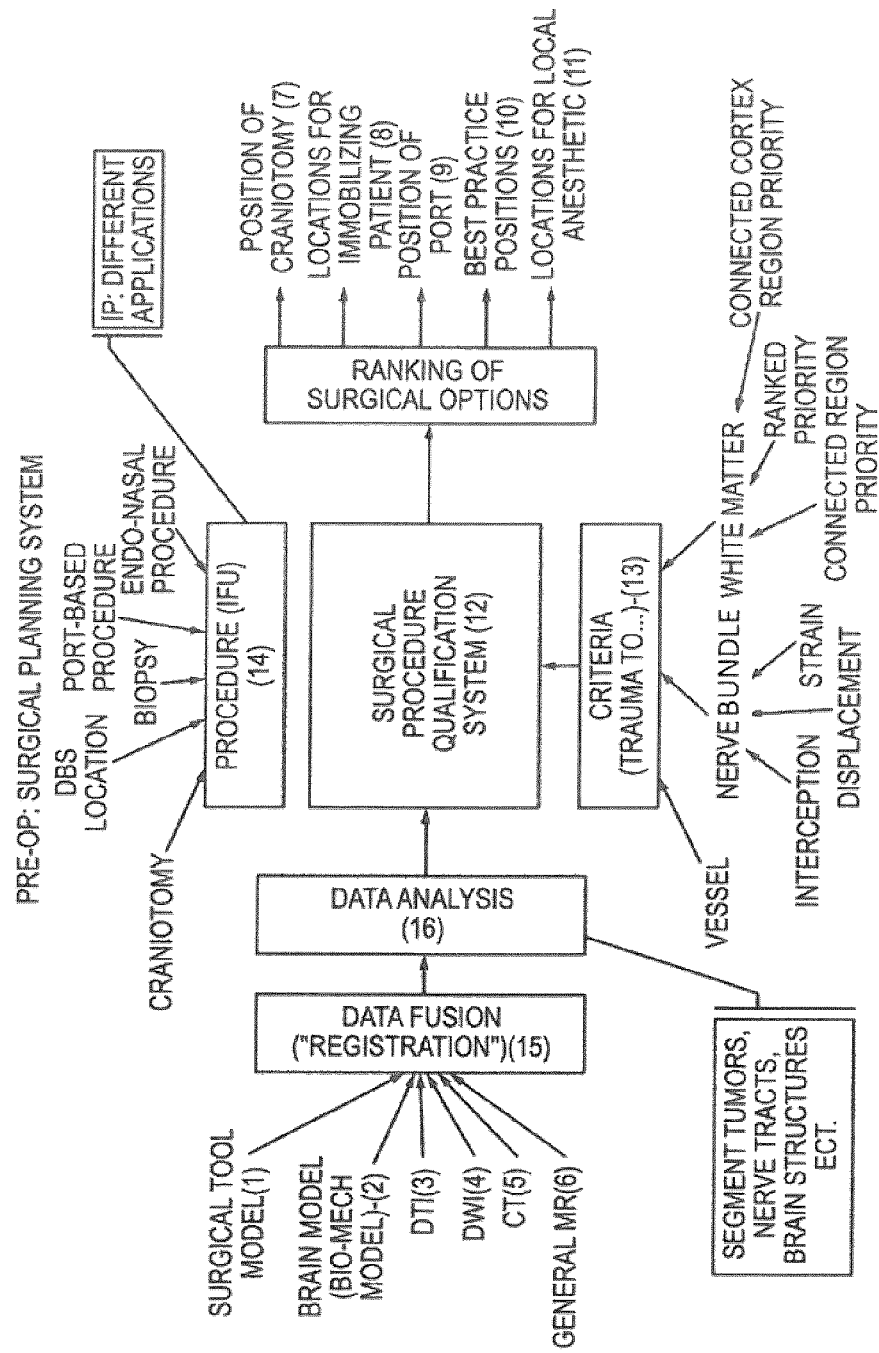
FIG. 2 is a block diagram showing system components and inputs for planning and scoring surgical paths as disclosed herein.
Figure 3:
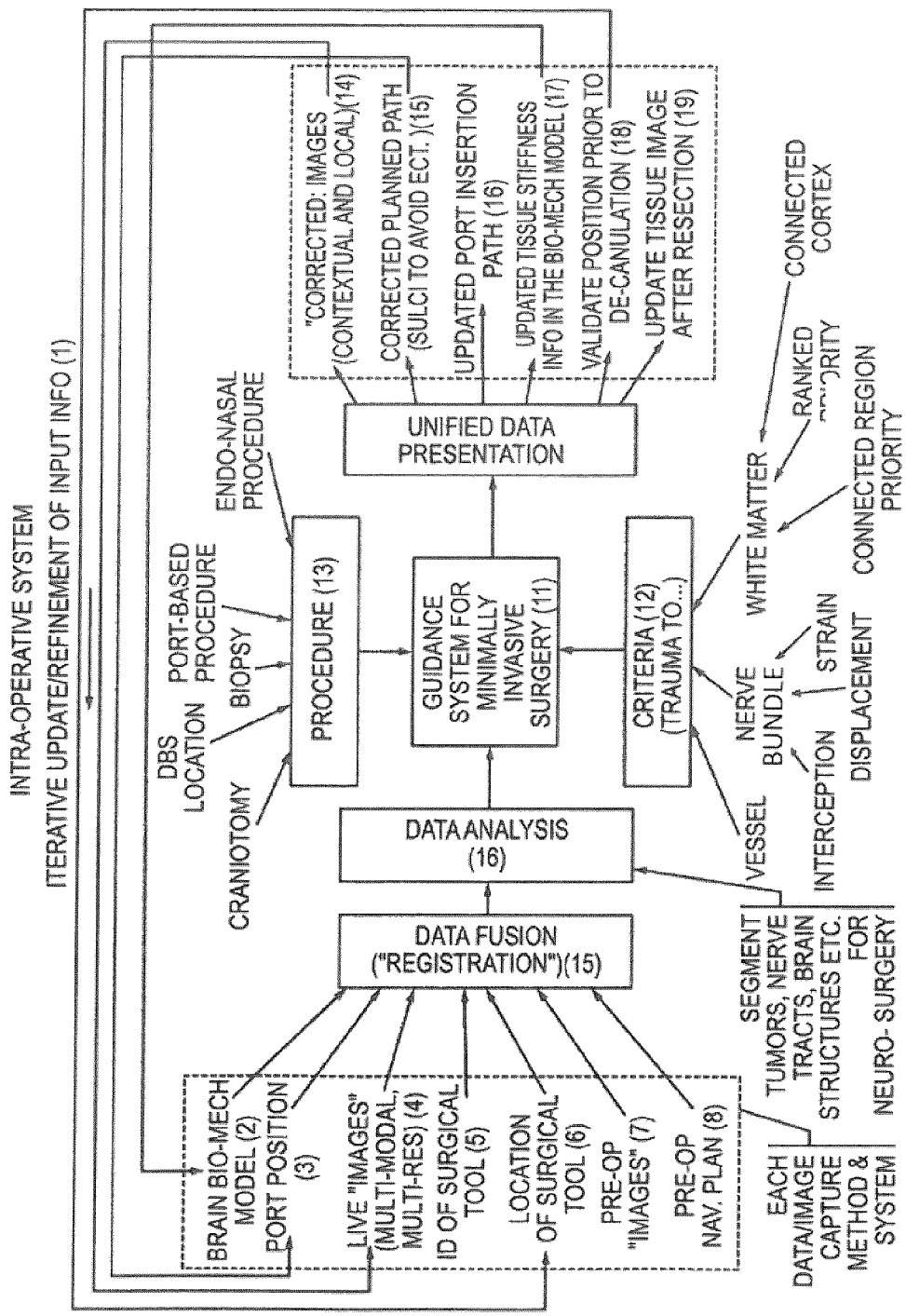
FIG. 3 is a block diagram showing system components and inputs for navigation along the surgical paths produced by an exemplary planning system of FIG. 2.

FIG. 2 is a block diagram showing exemplary system components and inputs for planning and scoring surgical paths as disclosed herein as disclosed in United States Patent Publication "PLANNING, NAVIGATION AND SIMULATION SYSTEMS AND METHODS FOR MINIMALLY INVASIVE THERAPY" as noted above. FIG. 3 is a block diagram showing system components and inputs for navigation along the surgical paths produced by an exemplary planning system of FIG. 2.

More specifically, FIG. 3 shows an embodiment for use as an intra-operative multi-modal surgical planning and navigation system and method. The system and method can be used as a surgical planning and navigation tool in the pre-operative and intra-operative stages. Persons of skill will appreciate that the data input(s) of the surgical planning steps and surgical procedures described in FIG. 2, can be used as input(s) to the intra-operative navigation stage described in FIG. 3.

The navigation system of FIG. 3 provides a user, such as a surgeon, with a unified means of navigating through a surgical region by utilizing pre-operative data input(s) and updated intra-operative data input(s). The processor(s) of system and methods are programmed with instructions/algorithms to analyze pre-operative data input(s) and intra-operative data input(s) to update surgical plans during the course of surgery.

For example, if intraoperative input(s) in the form of newly acquired images identified a previously unknown nerve bundle or brain track, these input(s) can be used to update the surgical plan during surgery to avoid contacting the nerve bundle. Likewise, if intraoperative data acquisition gives positional information about a known feature or tissue region, that measured position can be compared to the presumed location(s) of the pre-operative data and used to improve the correspondence. This comparison can be performed by the user, by means of visual comparison, or automatically using an energy minimization approach with appropriate metric. Persons of skill will appreciate that intraoperative input(s) may include a variety input(s) including local data gathered using a variety of sensor(s).

In some embodiments, the system and methods of FIG. 3 may provide continuously updated intraoperative input(s) in the context of a specific surgical procedure by means of intraoperative imaging sensor(s) to validate tissue position, update tissue imaging after tumor resection and update surgical device position during surgery.

The systems and methods may provide for re-formatting of the image, for example, to warn of possible puncture of critical structures with the surgical tools during surgery, or collision with the surgical tool during surgery. In addition, the embodiments disclosed herein may provide imaging and input updates for any shifts that might occur due to needle deflection, tissue deflection or patient movement as well as algorithmic approaches to correct for known imaging distortions. The magnitude of these combined errors is clinically significant and may regularly exceed 2 cm. Some the most significant are MRI based distortions such as gradient non-linearity, susceptibility shifts, eddy current artifacts which may exceed 1 cm on standard MRI scanners (1.5T and 3.0T systems).

Persons of skill will appreciate that a variety of intraoperative imaging techniques can be implemented to generate intraoperative input(s) including anatomy specific MRI devices, surface array MRI scans, endonasal MRI devices, anatomy specific US scans, endonasal US scans, anatomy specific CT or PET scans, port-based or probe based photoacoustic imaging, as well as optical imaging done with remote scanning, or probe based scanning.

The present system and method uses one or more sensors, wherein the sensor(s) detect information relating to a subject or patient's fiber tract model, interconnections between fiber tracts, as well as fiber tract elasticity. In some embodiments the sensors may be imaging sensors, such as diffusion weighted MRI devices which possess good fiber tract and fiber orientation detection capability, although it will be appreciated that other tissue sensors and imaging tools may be used (such as polarized light emission and detection). In some embodiments fiber elasticity at a given location (such as maps of elastic modulus to map tissue stiffness) can be directly measured; for example by various techniques such as imaging and direct physical measures. Some examples include magnetic resonance elastography, ultrasound elastography, optical coherence tomography, changes in reflected light polarization, and direct physical measures of exposed or biopsied tissue through, for example an array of strain gauges. In other embodiments, fiber elasticity at a given location of a fiber map can be determined based on known elasticity models of nerve (or muscle) fibers, and a segmentation of tissue categorization or type based on acquired images of the underlying tissue (For instance, Magnetic Resonance Imaging with T1 and T2 weighted imaging). The sensor(s) are in communication with one or more receiver(s) of a system that receives, records and/or processes the information regarding the fiber tract model and fiber tract elasticity input(s) detected by the sensor(s).

The systems and methods described herein measure or predict tissue and fiber deformation, based on properties of the fiber tract at a given location, for example, the local direction of each fiber tract at a given point. Persons of skill will appreciate, for example that tissues, particularly fibrous tissues, react differently when forces are applied transversely as opposed to laterally. Therefore, knowledge of a fiber tract's direction and interconnectivity can be useful in assessing fiber deformation at a given point when subjected to external forces. Further information regarding location of other tissues (such as cerebrospinal fluid, location and orientation of blood vessels, location and orientation of sulci), as detected through imaging (such as MRI, computed tomography and ultrasound) can be also incorporated into a deformation model by including known and measured stiffness and deformation properties of these tissue types.

In some embodiments, the system may include one or more processor(s) that analyzes the strain values on the fiber tracts, based on fiber tract elasticity model input(s) and event input(s), including force. By computing the effects of the event input(s)' forces at each location of the nerve fibers, strain values can be determined across the fibers. In some embodiments, strain values can be calculated at each location of each fiber tract, to determine fiber tracts at risk of shearing or other damage. This data can tend to be useful in surgical planning and navigation to avoid events or paths that can tend to exhibit higher damage risks.

In some embodiments, readings and calculations can be repeated on an iterative basis, as event input(s) change, for example as a probe's position changes during a surgical procedure. This can tend to be advantageous to provide real-time intraoperative surgical information.

In other embodiments, sensor(s) can tend to detect the brain tissue type in a particular location, such as white and grey matter, for example. Known properties of the various tissue types, such as myelinated or non-myelinated, can be included as input(s) to provide additional values for measuring deformation.

In further embodiments, Fractional Anisotropy ("FA") information, measured by sensor(s) including diffusion weighted MRI devices ("DWI"), may be used as input(s) to determine fiber tract strength and oriented stiffness at a given location. For example, when FA input(s) are near 0, diffusion of water detected by a DWI imaging sensor tends to be isotropic (e.g. equally restricted in all directions). When FA approaches 1, the diffusion of water detected by a DWI imaging sensor tends to occur only along one direction and is completely restricted in all other directions. Such information can be used to map the degree of oriented stiffness of a fiber tract at a particular point.

In still further embodiments, sensor(s) can detect additional input information for use in detecting tissue deformation. For example, location points where sulci or cerebrospinal fluid interface with the tissue of interest can be used to adjust calculations for surrounding tissue stiffness, as these interfaces can introduce additional considerations at the location point affecting elasticity and deformation.

In use, the embodiments may tend to be used for preoperative surgical planning, intraoperative surgical navigation, and post-operative educational review of a procedure, such as for a surgeon self-assessment and student education and review, and retrospective determination of deformation of points of interest for subsequent imaging and follow-up assessment.

Referring again to FIG. 1, once the plan has been imported into the navigation system (step 102), the patient is affixed into position using a head or body holding mechanism. The head position is also confirmed with the patient plan using the navigation software (step 104). In this embodiment, the plan is reviewed and the patient positioning is confirmed to be consistent with craniotomy needs. Furthermore, a procedure trajectory may be selected from a list of planned trajectories produced in the planning procedure.

Returning to FIG. 1, the next step is to initiate registration of the patient (step 106). The phrase "registration" or "image registration" refers to the process of transforming different sets of data into one coordinate system. Data may be multiple photographs, data from different sensors, depths, or viewpoints. The process of "registration" is used in the present application for medical imaging in which images from different imaging modalities are co-registered. Registration is necessary in order to be able to compare or integrate the data obtained from these different modalities.

Those skilled in the art will appreciate that there are numerous registration techniques available and one or more of them may be used in the present application. Non-limiting examples include intensity-based methods which compare intensity patterns in images via image metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, for example, a series of MR images can be co-registered, while multi-modality registration methods are used to register images acquired by different scanner/sensor types, for example in MRI and PET. In the present disclosure multi-modality registration methods are used in medical imaging of the head/brain as images of a subject are frequently obtained from different scanners. Examples include registration of brain CT/MRI images or PET/CT images for tumor localization, registration of contrast-enhanced CT images against non-contrast-enhanced CT images, and registration of ultrasound and CT. The process should not be confused with the registration of navigational hardware to a reference frame relative to the patient. Both procedures are necessary to compare physical locations in the OR to data sets and images generated pre-operatively.

Once registration is confirmed (step 108), the patient is draped (step 110). Typically draping involves covering the patient and surrounding areas with a sterile barrier to create and maintain a sterile field during the surgical procedure. The purpose of draping is to eliminate the passage of microorganisms (i.e., bacteria) between non-sterile and sterile areas.

Upon completion of draping (step 110), the next steps is to confirm patient engagement points (step 112) and then prep and plan craniotomy (step 114). Upon completion of the prep and planning of the craniotomy step (step 112), the next step is to perform the craniotomy procedure (step 114) where a bone flap is temporarily removed from the skull to access the brain (step 116).

During the process of craniotomy (step 116) and any subsequent steps thereafter, there is a risk of tissue deformation. The brain is housed in the skull and is under constant intracranial pressure; the brain will change shape if there is a fluctuation in pressure. Any puncture to the skull (i.e., through drilling or cutting of the skull) may cause fluid release and the change in pressure may change the shape of the brain. Further, during and after craniotomy (steps 116 to 130) if the incision in the dura is large, or if the dura is under pressure due to fluid, more deformation may result during the dura incision. Brain tissue deformation may also occur during cannulation (step 134) when a device (e.g. a surgical port) and instruments are inserted down a sulcal path of the brain. Further, during craniotomy (step 116), registration data is also being updated with the navigation system in real time (step 122). While the present method does not involve modeling this type of deformation, it will be appreciated that in the event that a pressure model is generated, then the intracranial pressure needs to be taken into account.

The next step is to confirm the engagement within craniotomy and the motion range (step 118). Once this data is confirmed, the procedure advances to the next step of cutting the dura at the engagement points and identifying the sulcus (step 120). Registration data is also updated with the navigation system at this point (step 122).

Figure 4A:
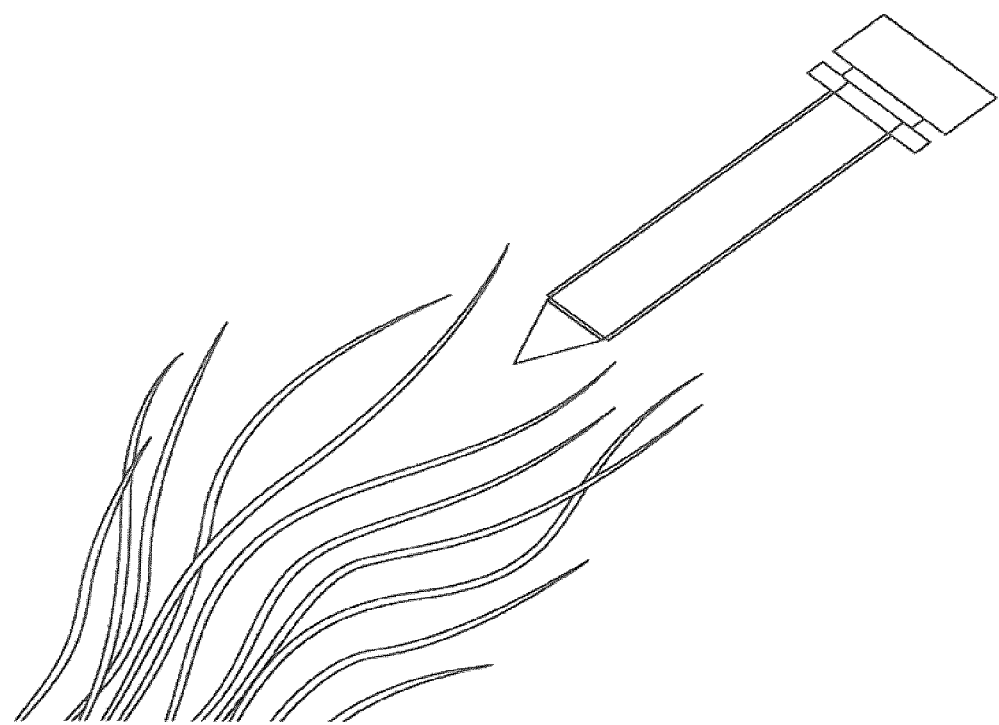
FIG. 4A is a diagrammatic representation of pre-cannulation.
Figure 4B:
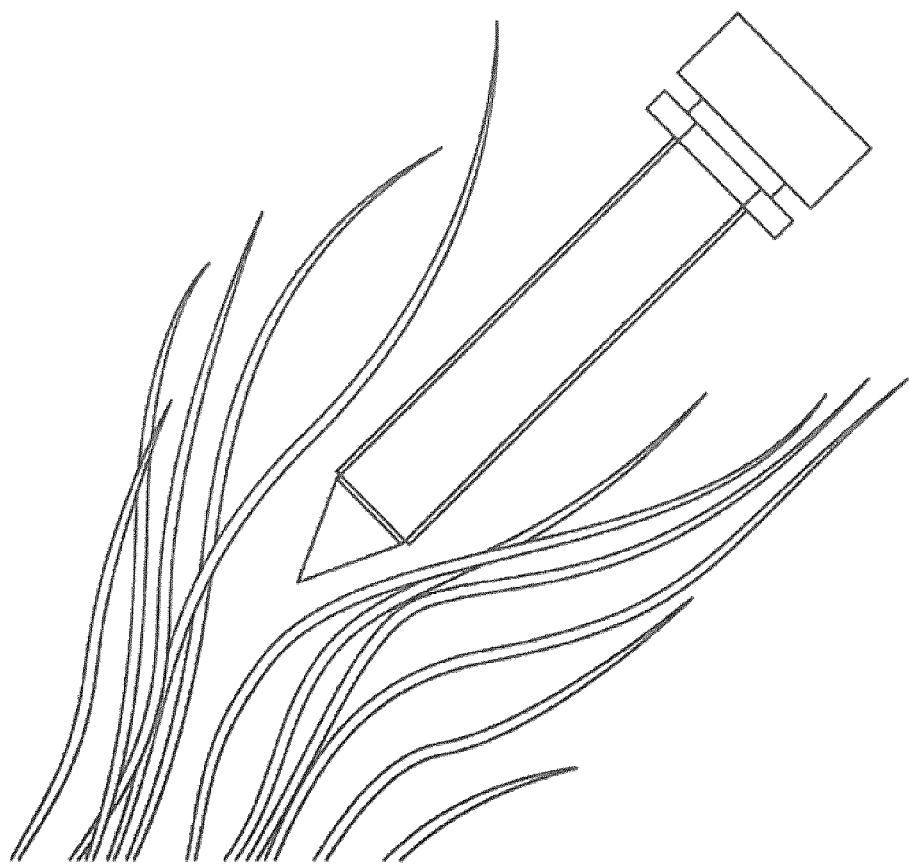
FIG. 4B is a diagrammatic representation of post-cannulation.

Thereafter, the cannulation process is initiated (step 124). Cannulation involves inserting an instrument (e.g. surgical port) into the brain, typically along a sulci path as identified in step 120, along a trajectory plan. Cannulation is an iterative process that involves repeating the steps of aligning the port on engagement and setting the planned trajectory (step 132) and then cannulating to the target depth (step 134) until the complete trajectory plan is executed (step 124). FIG. 4A is a diagrammatic representation of pre-cannulation, while FIG. 4B is a diagrammatic representation of the same port after cannulation, where some fiber tracts have been displaced during the process.

Once cannulation is complete, the port introducer is removed. The surgeon then performs resection (step 128) to remove part of the brain and/or tumour of interest. Next de-cannulation (step 126) is performed by removing the port and any tracking instruments from the brain. Finally, the surgeon closes the dura and completes the craniotomy (step 130).

The present disclosure provides a method for producing an evolvable tissue model of a patient undergoing a medical procedure. The method includes obtaining at least one set of input data of the tissue of the patient that will undergo the procedure. This set of input data includes therein directional data of at least one component of the tissue (it is noted that directional information of more than one tissue component may be used in more sophisticated models but a basic model requires the directional information of at least one tissue component). Such directional information could be inherent to the material, or it could represent directional information about the surface interface(s) of the material. For example, if the tissue being operated on is the brain, it is noted that in the brain sulci are convolutions of the white matter surface that extend into the volume of the brain. As such, they form natural, oriented tissue boundaries and the properties of these sulcal boundaries will affect the deformation of white matter if a tool is introduced near or within them.

It will be appreciated that the tissue model, in its simplest form, can be constructed using the directional information of at least one tissue component, but a more sophisticated model may be produced using the directional information of more than one type of tissue in the tissue volume being operated on, as well as non-directional information about the tissue location, constituents, etc. This input data may be obtained in several ways, for example it may be images obtained by various imaging modalities (e.g. MRI, CT, X-ray, ultrasound, Doppler ultrasound, functional MRI, etc.) having with appropriate natural dimensions (e.g. 2D, 3D, 2D+time, 3D+time, etc.). Alternatively, instead of images the inputs may be other data sets of interest, such as spectrographic (e.g. oxygen concentration in a region via NIR spectrography), biomechanical (stiffness or density measure at a point or region), electro-magnetic (e.g. Electroencephalogram), optical (microscopy), or physical (such as pressure, fluid flow rates etc.). Specific detailed approaches may be used including, but not limited to, using any of magnetic resonance diffusion weighted imaging and its specific detailed approaches such as diffusion tensor imaging, q-ball, HARDI etc.; or interferometric approaches such as OCT; or algorithmic segmentation and analysis of cellular orientation image data (such as microscopy).

Prior to producing the model, the directional information needs to be in a usable format. If the directional information as acquired is already in a usable format as received then the model may be generated. In the event the directional information is not usable as is, then prior to constructing the model a step of preprocessing the input data and extracting therefrom directional information of the at least one component of the tissue in a usable format is carried out.

Non-limiting examples of formats that may used to represent the directional information of the at least one component of the tissue includes, but is not limited to, an image format, and/or a geometric model, and/or a scalar field, and/or a vector field, and/or a tensor field, and/or a representation of angular components such as via quaternion or rotation matrices, and/or a decomposition of angular components via any appropriate basis such as spherical harmonics, and/or any generalized functional representation of directional orientation.

When the model is first produced using pre-operative images prior to physically accessing the tissue site, MR based diffusion tensor imaging (DTI) may be used to provide images from which directional information of at least one tissue component can be obtained. For example in the case of muscle tissue, tendon and ligaments, the directional properties of the tissue can be discerned. Similarly, in the case of neurosurgery, the directional properties of fiber tracts can be elucidated from pre-operative DTI. For updating the model intraoperatively, or producing a new base model in the event of significant deformation, other imaging modalities may be used. These include optical inspection of fiber locations (via endoscope or microscope), and spectroscopy, intraoperative MRI, and ultrasound imaging and elastography.

After the input data has been obtained and received, the method includes preprocessing the input data and extracting from it directional information of the particular component of the tissue for which the information has been obtained. This direction information of the particular component of tissue is then represented in a pre-selected format. Non-limiting examples of the format in which the directional information is represented range from the simple (e.g. purely geometric models such as connected line segments with rigid interactions) to the general (e.g. finite element modeling). The choice of representation is driven by the interactions to be modeled. For example, if the only information available is a geometric representation of fiber tracts, deformations could be modeled as mass-spring interactions on piecewise linear elements of the tracts. However, if additional information is available it may be beneficial to measure tissue homogeneity, or pressure, or fluid dynamics, etc. In this case such a geometric model is far too simple and a more general setting such as finite element modeling (or other PDE methods), or energy methods (e.g. Gibbs/Markov random fields), or more general statistical modeling.

Using this presentation of the directional information, an oriented tissue map is produced which reflects the directionality of the particular tissue component. The oriented tissue map then forms at least one constituent that is used to produce a tissue model such that the tissue model reflects the directionality of the at least one tissue component. This gives an evolvable tissue model such that when the tissue model is subjected to an influence that causes some sort of discernable transformation of the tissue (the evolution of one or more physical properties over time, one example being tissue deformation) over a period of time, the tissue model directionally informs the transformation (e.g., deformation) over that period of time in a manner which reflects a trajectory of the influence interacting with the directionality of the particular tissue component.

It is noted that the tissue model may be produced with many constituents (which may or may not exhibit anisotropic behaviour) in addition to the oriented tissue map, but the presence of the oriented tissue map is a necessary component of the oriented tissue model, since its presence allows modelling of any tissue deformation with realistic constraints reflecting the directionality of the particular tissue. Examples of other constituents that may be used to produce the evolvable tissue model includes any one or combination of physical or biomechanical properties of any one or combination of constituents of the brain and head, for example grey matter, white matter, cerebral spinal fluid, ventricles, brain stem, meninges, vasculature, tumor, bone, sulcal structure and morphology, fiber tracks and brain and/or head segmentation maps, lesion and pathology segmentations.

It will be understood that in addition to the oriented tissue map, the model may include other components. For example, non-limiting examples of other constituents which may be used to build the tissue model include, but are not limited to, any one or combination of elasticity properties of the at least one tissue component and/or other tissue components, tensile properties of the at least one tissue component and/or other tissue components, pressure properties of the at least one tissue component and/or other tissue components, as well as segmentations of various tissue type(s) relative to any of the input data sets and the associated boundaries between tissue types (e.g. grey matter, white matter, CSF and sulcal locations), vasculature, fluid representations (e.g. CSF, blood, edema etc.), skeletal or musculoskeletal representations, skin and/or other organs as geometric models.

The following examples are illustrative only. If the influence to which the model is being subjected is a surgical instrument interacting with the tissue model, the model deforms in a manner consistent with the angle that the instrument intersects the tissue. For example, if the instrument intersects the oriented tissue parallel to the directionality of the tissue, the deformation of the model will be different compared to the situation of the instrument intersecting the tissue model perpendicular to the directionality of the tissue. Likewise, if a region of tissue is compressed or deformed such that it interacts with another region of tissue, the directional components (or lack thereof) of these regions will affect the interaction; for example muscle fibers being pressed into another muscle, or fiber tracts in brain being displaced into other, non-connected fibers.

The present evolvable tissue model may be coupled with any type of influence in order to model deformation of the tissue due to the impact of the influence on the model. Various examples of influence include, but are not limited to, the effect of surgical instruments penetrating into the tissue, swelling of the tissue, pressure changes, tissue resection, drainage, cauterization, bleeding, and boundary changes such as due to opening a skull flap or craniotomy.

The method of producing an evolvable tissue model may be used to model deformation of any part of the anatomy (human or animal) in which at least one tissue constituent exhibits directional features.

Figure 5:
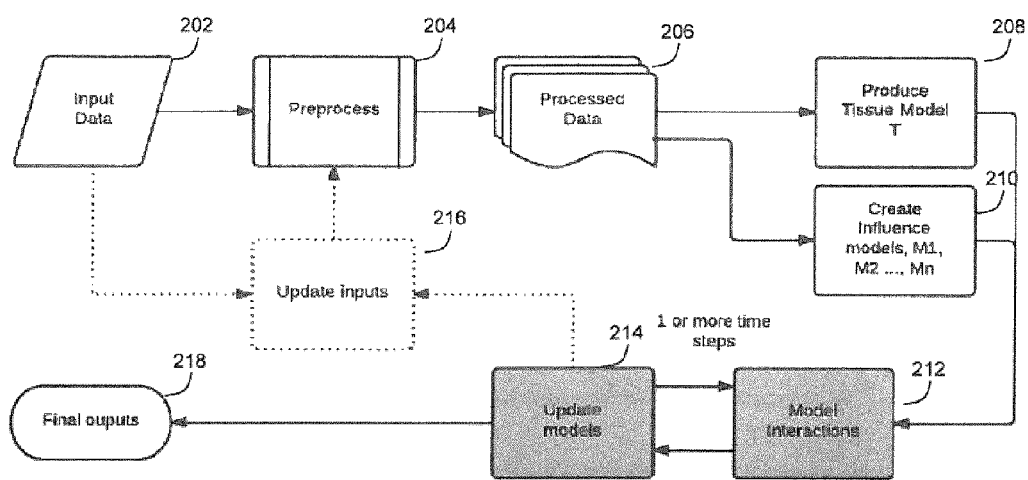
FIG. 5 is a flow chart illustrating a general flow for detecting fiber tract deformation.

FIG. 5 is a flow chart illustrating a general flow for producing a tissue model and deformation. The first step in FIG. 5 is to receive input data (step 202) on at least tissue orientation but can also include more data, for example data on connectivity with surrounding tissues. The input data may consist of any form of data received from cameras, sensors, tracking tools, navigation systems, MRI, ultrasound or other known modalities. Input data from step 202 may also include various influences, for example known perturbations or known events, based on modeling historical data, as additional input(s). These event input(s) may include, for example, a pressure drop in a region of the subject's tissue where a surgical procedure is performed, insertion of a surgical tool or foreign object into the surrounding tissue, such as a surgical port, or negative pressure due to tissue resection during a biopsy. Persons of skill will appreciate that various different events could affect the deformation of tissue at a given location in the subject's body.

After data is received at step 202, the system then preprocesses the data in step 204 to generate a possible set of data which are organized and presented in an appropriate data format 206. With respect to the input data relating to the tissue, in one embodiment this format will present at least data regarding at least tissue directionality, namely an oriented tissue map, but may also include other information, including but not limited to, the tissue elasticity input(s) or other quantifiable metrics detected by the sensor(s). Thus the pre-processing step (step 204) in FIG. 5 is responsible for receiving the input data, including input data on the tissue and influences that will be applied to the tissue model.

Upon completion of the pre-processing (step 204), the formatted data for the tissue data input and the influence(s) are used to simultaneously produce a tissue model (step 208) and influence model(s) (step 210). As noted above, influence models may be comprised of any received inputs that may influence the tissue. Influence models may include parameters from tracking tools, ports and pressure models as examples. Input data that affects tissue displacement (e.g. shape of tool being inserted) affects the influence model and input data that defines the tissue being displaced affects the tissue model.

The next steps in FIG. 5 involves a cyclical loop consisting of 1 or more iterations of model interactions (step 212) and updating the models (step 214). This iterative process typically involves how one or more influences on the model results in deformation of the tissue, over a specified period of time. Upon completion of the model updates (step 214), the (intermediate or final) output (step 218) is captured. Additionally, the input data (step 202) and update model (step 214) step may update the inputs (step 216) and feed these updated input results back into the pre-process step (step 204). It is noted that the (final or intermediate) output will always depend on a) what one is modeling, and b) what the models are. Non-limiting examples of what may be modeled include forces applied at particular positions over time, such as mechanical forces or pressure, and similarly such properties on vector fields, meshes, or other representations. Additionally, material properties such as stiffness or viscosity may be changed by evolution of the model(s) or asserted. Furthermore, it may be advantageous to represent approximations of such values on individual elements as averaged behaviour or immutable values, etc., when applying them as boundary conditions or at a distance.

Non-limiting examples of what such models may include are systems of equations (e.g. PDE or ODE systems), energy functions, boundary conditions, vector fields or stress/strain tensor fields, deformation fields, and the geometric representations (such as line segments, rays, lattices or meshes) needed to support them. Additional regional information in the form of labeling maps, segmentations, regions of interest, or other metadata may be provided as input to the modelling.

Those skilled in the art will appreciate that the precise nature and approach to modeling such interactions will depend on the available data and the interactions being modeled. Non-limiting examples include optimization methods, statistical estimation, energy minimization methods, numerical simulation of ODE/PDE systems, etc.

As a simple example, if the effect of a surgical instrument inserted into the tissue is being modelled, the influence model will at a minimum include the dimensions and shape of the instrument penetrating the tissue, and the iterative process will involve movement of the instrument a given distance in a given period of time, with the output 218 showing the amount of tissue deformation at a selected time. A more detailed example will be given below with respect to FIG. 6.

Once the tissue model is produced, it may be stored in the storage device of the computer processor for future reference and/or displayed on a visual display device. In addition, the tissue model may have visual clues assigned to the various constituents of the tissue model. For example, colors may be assigned to different tissues or other constituents of which the model is comprised, boundaries between the regions may be represented as surfaces to display, the time evolution of the tissue model (once modeled) may be animated.

EXAMPLE

Medical Procedures Involving the Brain

Figure 6:
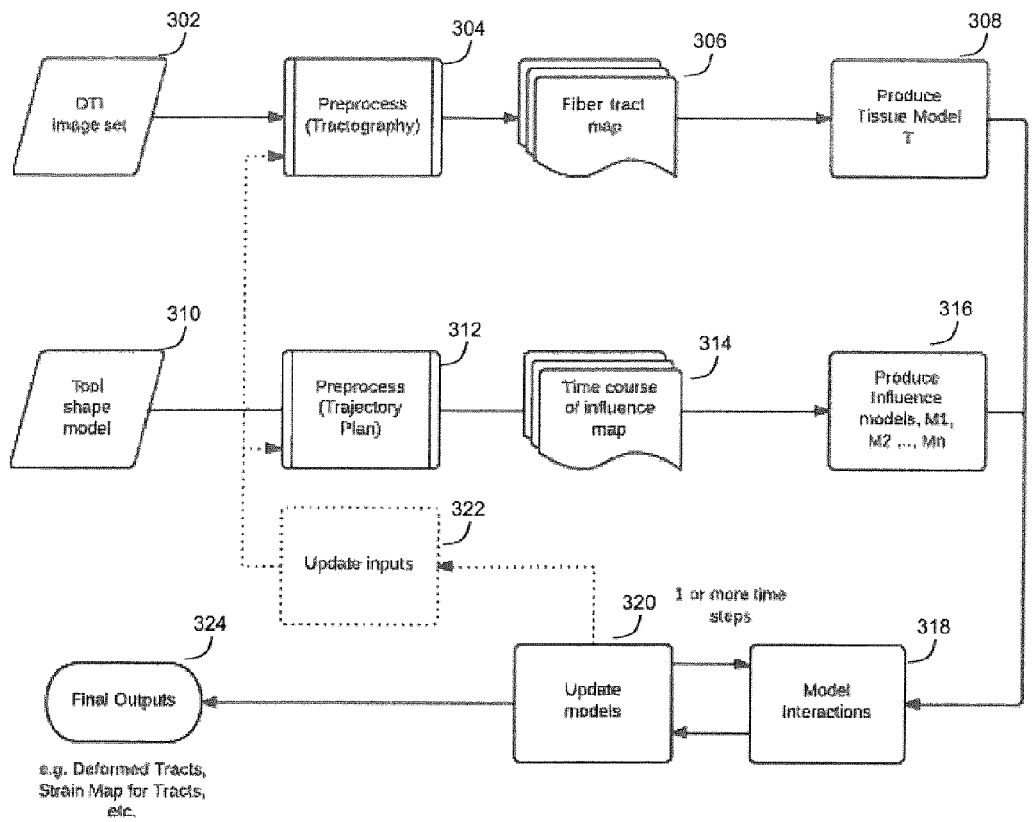
FIG. 6 is a more detailed flow chart illustrating modeling of fiber track deformation incorporating DTI images and tool image models.

FIG. 6 is a flow chart illustrating the present method of modelling fiber tract deformation incorporating DTI images and surgical tools shape models. FIG. 6 is an embodiment of a specific case of producing a fiber tract deformation model only and does not involve other tissue types as illustrated in FIG. 5. In FIG. 6, two data streams, including DTI image data (step 302) and tool shape model (step 310) are received as input data.

After the DTI image set data is received (step 302), the system then preprocess the data (step 304), typically using a streamline tractography algorithm. After preprocessing (step 304), a fiber tract map (step 306) is created. The fiber tract map produced in step 306 is then used to produce a tissue model (step 308).

Figure 7:
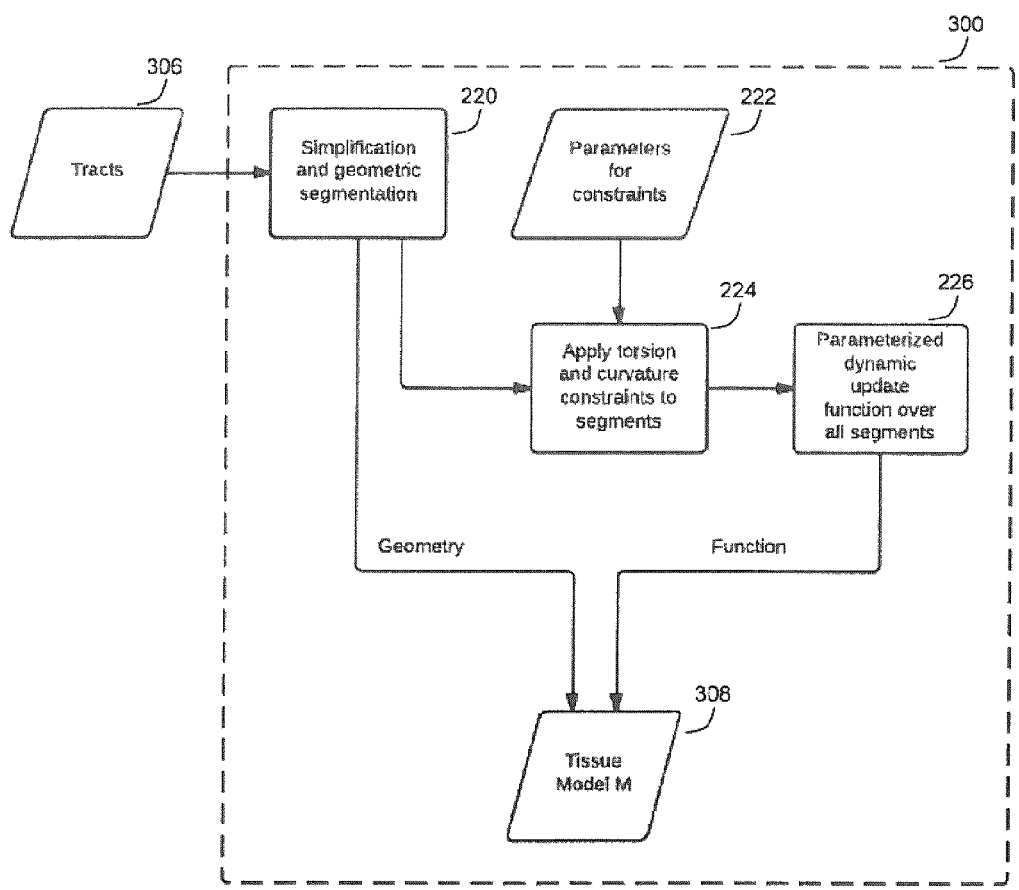
FIG. 7 is a flow chart further elaborating on the "Create Tissue Model" step 308 as outlined in FIG. 6.

FIG. 7 is a flow chart further elaborating on the "Create Tissue Model" step (308) as outlined in FIG. 6 with details of the sub-steps involved being shown in dotted box 300. In FIG. 7, processed tracts are received as produced in step 306 as an input into the create tissue model (step 308). Step 308 may be further divided into four sub-steps (box 300). The first sub-step involves simplification and geometric segmentation (step 220) of the tracts. For example, the geometry can first be simplified using the Douglas-Peucker algorithm, then polylines deemed too short can be removed. Following this, all the polylines may be re-sampled into equally spaced segments, to simplify model updates.

Referring again to FIG. 7, the geometric segmentation (from step 220) is then used to apply to torsion and curvature constraints to segments (step 224) where trained parameters for constraints (step 222) may be used as inputs. For example, a simple version of this would proceed as follows. Each segment is considered to be rigid and non-compressible. We apply a simple parametric differential model to their motion, e.g. a mass-spring model. By parameterizing the motion in terms of Frenet frame of reference, motion in the osculating plane and normal plane may be constrained separately. For example, we can parameterize resistance to curvature and torsion separately (see, e.g. Spivak, A Comprehensive Introduction to Differential Geometry for these standard properties). The parameters for the model are applied in step 224; these could be arrived at in many ways, e.g. via empirical measurement, reference to studies on measurable properties of the tissue in question, or direct intra-operative measurements. The parameters may also be improved or "trained" also by reference to intraoperative positioning of the tissue and comparison to modeled results. The result is a parameterized dynamic update function for each segment forming (step 226) a mapping of how each segment will behave under external influence.

The tissue model is produced using both the geometrical and parametric (e.g. functional) inputs. Specifically the tissue model is dependent on both the orientation and structure of the tract segments (as processed through 222, 224 and 226) as well as the relative position of one tract segment to the others (since this is how forces are transferred either longitudinally through the segment or by the segment encountering another geometric feature as it moves). Thus the geometry plus the parameterized model created for it form the "tissue model".

A more complicated approach would involve more models, for example a rigid model of the skull could be added as hard constraints on the movement of the geometry. Going further towards a general solution, given suitable inputs a finite element model (FEM) incorporating all material in the volume of interest can be created. A simple version of this would require only a labeling of all tissue types, and a tessellation of the volume into a suitable mesh capturing the interfaces of white matter, grey matter, cerebrospinal fluid and air as an example. Given such inputs, as well as, the tractography geometry described previously, it is possible to introduce anisotropic weighting of the PDE equations in the finite elements that are intersected by fiber tracts and thus introduce tissue orientation to the modeling.

In addition to this Produce Tissue Model (step 308 via steps 302, 304 and 306), a parallel processing path involving tools (i.e., port, tracking tools, etc.) is also pursued. Tool shape model (step 310) is used as input data. The tool shape model undergoes preprocessing (step 312) where a trajectory plan is incorporated. This trajectory plan can be any parametric curve in space, beginning at an entry point and ending at a target, and is provided by the user. This curve is then parameterized by time (step 314), the simplest version of this would be to uniformly step along the curve for a given total time, but non-uniform stepping could also be used. The user will provide this time variable, or it can be automatically created for them if they provide a total time. This (time) parameterized trajectory of the geometric shape is given a (nominal, in the simplest version, or this can also be parameterized in time) force, and hence forms the influence model (step 316).

Both the tissue model production (step 308) and the influence models (step 316) are used as inputs into a cyclical loop comprised of 1 or more iterations of model interactions (step 318) and updating the models (step 320). Upon completion of the model updates (step 320), the final output (step 324) consisting of such results as deformed tracts and strain map for tracts are created. A further elaboration on this can be found in FIG. 8 and is described below for more detail.

Finally, this system has an update loop where at the update model step (step 320), the system updates the inputs (step 322) and feeds these updated input results back into the preprocess step (steps 304 and 312) respectively. This (optional) update loop allows dynamic update of the tractography map and/or tool shape (e.g. if deformed by internal pressure from the tissue) to be incorporated in the deformation computation. If these inputs are considered static or constant then the entire model can be updated through repeated looping time steps between 318 and 320, with no need to recourse to the outer loop. An example of the more general case would be if we have introduced a robotic tool with appropriate sensors, the tool will provide data including changes to its position, attitude and joint positioning. These measurements can provide dynamic updates to the influence model, facilitating the updating described in 322. Those skilled in the art will appreciate that this could also be done from modeled estimation of tool position and or shape, and that further information could be derived from other sensors (e.g. Bragg gratings or other interferometric approaches, bend sensors, etc.).

Figure 8:
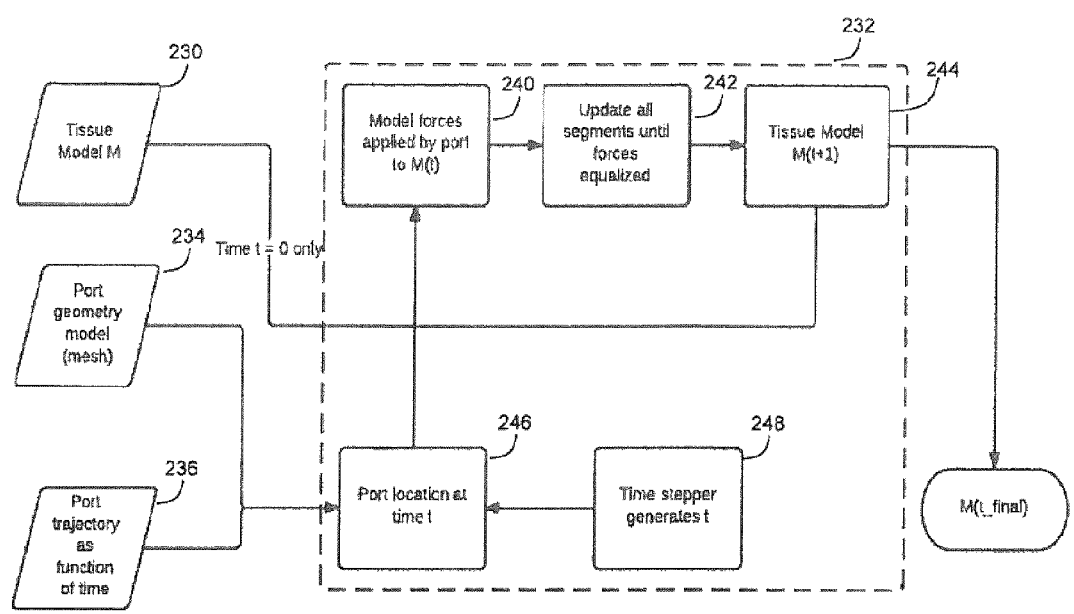
FIG. 8 is a flow chart further elaborating on the "Model Interaction" and "Update Model" steps 318 and 320 as outlined in FIG. 6.

FIG. 8 is a flow chart further elaborating on the "Update Model" and "Model Interaction" steps outlined in FIG. 6. The model interactions (step 212) and update models (step 214) steps from FIG. 6 consists of sub-steps as outlined as elements in box 232 in FIG. 8.

In FIG. 8, tissue model (step 230) is introduced at an initial time (e.g., time t=0). A port geometry model (step 234) which may consist of a mesh file (e.g. an ".stl" file or a computer aided design (CAD) drawing) is received as an input. A further input of a port trajectory (step 236) is also received. The port trajectory in step 236 may already be a positional function of time, such as the trace of an intraoperatively inserted instrument as tracked by a surgical navigation system, or may consist of a contemplated surgical plan under assessment in a surgical planning software system, in which case it will be automatically parameterized uniformly over a nominal time to create the trajectory as a function of time. The port geometry (step 234) and port trajectory (step 236) are combined to determine a port location at any specific time.

A time stepper module is used to generate the time "t" (step 248) and is also used as an input to determine port location (step 246) at a specific time. In this simple model, the port location is determined entirely by its defined trajectory, and the tissue deforms around it. More complex modeling could allow the modelled tissue forces to affect the port position, causing the port location to be the result of its insertion forces and the resistive forces of the tissue it affects. The time stepper (step 248) is typically a software function with a graphical user interface (e.g., a slider or button control with automatic "playback") and is used to generate steps along the path, though it may also be taken from actual measured instrument movements measured directly during a surgical procedure by a tracking system. Further, the time stepper (step 248) is typically a time variable that is used to drive the simulation steps. In the exemplary embodiment, time steps may be uniform (e.g., $t_1$=1 second, $t_2$=2 seconds, $t_3$=3 seconds, etc.), but alternate embodiments may consider steps to be non-uniform to represent different phases during the path (e.g., $t_1$=1 second, $t_2$=3 seconds, $t_3$=25 seconds, etc.). The time variable may or may not correspond to "clock time" during the procedure.

For any given step, once the port location at time $t_n$ is determined (step 246), the delta between this and the ports position at time $t_{n-1}$ can be computed and each segment of the tissue model evaluated to see if it is affected by this motion. For each affected segment, model forces are applied by the port to the segment (step 240) where the model evolves over time (t). Thereafter, the system updates all segments of the model until all forces are equalized (step 242). The model then advances to the next step at time=$t_{n+1}$ (step 244) where it then interacts with the next step of the port. The model is constantly being updated and continues in this cyclical loop until the system time step has reached the end of the planned course of the port.

In more complex embodiments, the output of the inner loop 232 can be compared with the original position of the models to update the inputs with estimations of their evolution over time. For example, by keeping track of the motion of every segment in the geometric tissue model described above and averaging their motions over a discrete volume enclosing them, we can arrive at a vector valued deformation field (whose magnitude is 0 wherever no geometric motion was observed). This deformation can then be cleaned up (e.g. to enforce a diffeomorphism) if desired. The resultant deformation can then be applied directly to any input image volumes as desired. For example this could be used to estimate a T1 weighted image part way through the procedure from pre-operative data. Furthermore, the deformation can be applied to the input entire data and used to regenerate a new geometric model from the modified images.

This updated model can be used in diverse ways. For example, it can be compared to the result of the geometric model for regularization purposes or to estimate modeling errors, used as input for a new cycle of model updates, and/or it may presented to the user on a visual user interface. This approach obviously generalizes to more sophisticated tissue models. Additionally, influence models may be treated the same way. In the simple example, geometry used (i.e. the port) to influence the tracts was considered to be purely rigid, but in general all of the influence models may be modified by the tissue as well, and the model update step described here may affect influence models as well as tissue models. For example, if a DBS (deep brain stimulation) introducer, or similar artifact, is used as an influence model its shape may be modeled and distorted by the resistance of the tissue. By adjusting its planned trajectory into the brain under the action a deformation field such as described here, we can compare the modeled position to the deformation of the original plan and present metrics based on its divergence to the user.

It will be appreciated that the method for producing the evolvable tissue model may form a stand-alone product for use by clinicians looking to produce general or specific tissue models and has utility in and of itself and may be stored in a computer readable storage medium. Furthermore, the method of modelling the effect of an influence on tissue using an evolvable tissue model form a stand-alone product for use by clinicians looking to model the effect of influences using a tissue model specific to their needs may be stored in a computer readable storage medium by itself. In addition, both the method for producing the evolvable tissue model and the method of modelling the effect of an influence on tissue using the evolvable tissue may be combined into a single package and may be stored in combination on a computer readable storage medium.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, C#, JavaScript, SQL, or any other suitable programming language and may comprise modules, classes or other functional units of code as will be appreciated by those skilled in the art. At least some of the elements of the system that are implemented via software may be written in assembly language, machine language or firmware as needed. In any case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Therefore what is claimed is:

1. A method for producing an evolvable cerebrospinal tissue model of a patient, comprising the steps of:
    a) receiving at least one set of diffusion imaging input data of cerebrospinal tissue of a patient, said at least one set of input data containing at least directional information with respect to diffusion fiber tracts;
    b) representing the directional information of the at least one component of cerebrospinal tissue in a pre-selected format and producing therefrom an oriented fiber tract tissue map; and
    c) producing a cerebrospinal tissue model in which at least one constituent of the cerebrospinal tissue model uses the oriented diffusion fiber tract tissue map such that the cerebrospinal tissue model reflects the directionality of the diffusion fiber tracts so that when the cerebrospinal tissue model is subjected to an influence any evolution of the cerebrospinal tissue model over time incorporates the directionality of the diffusion fiber tracts, and wherein at least one additional constituent of the cerebrospinal tissue model uses the oriented diffusion fiber tract tissue map such that the cerebrospinal tissue model represents any one of elasticity properties of the one or more tissue components, tensile properties of one or more tissue components or pressure properties of one or more tissue components as a geometric model.

2. The method according to claim 1 wherein step b) is executed using the directional information as acquired when said directional information is usable in a format as received in step a), and wherein in the event the directional information is not usable as is, including a step of preprocessing the input data and extracting therefrom directional information of the at least one component of the tissue in a usable format.

3. The method according to claim 1 wherein the cerebrospinal tissue model includes further constituents, said further constituents including any one or combination of the segmentations of various tissue type(s) relative to any of the input data sets and associated boundaries between tissue types, vasculature, fluid representations, skeletal or musculoskeletal representations, skin and/or other organs as geometric models.

4. The method according to claim 1 wherein the preselected format used to represent the directional information of the at least one component of the cerebrospinal tissue includes an image format, and/or a geometric model, and/or a scalar field, and/or a vector field, and/or a tensor field, and/or a representation of angular components such as via quaternion or rotation matrices, and/or a decomposition of angular components via any appropriate basis such as spherical harmonics, and/or any generalized functional representation of directional orientation.

5. The method according to claim 1, including visually displaying the cerebrospinal tissue model.

6. The method according to claim 1 wherein the cerebrospinal tissue model of the patient's brain includes further constituents, said further constituents including any one or combination of physical or biomechanical properties of any one or combination of constituents of the brain and head.

7. The method according to claim 3 wherein the boundaries between tissue types includes boundaries between any combination of grey matter, white matter, cerebral spinal fluid, sulcal locations, tumor, bone, meninges, vasculature, and ventricles.

8. The method according to claim 3 wherein the fluid representations include cerebral spinal fluid, blood, and edema.

9. The method according to claim 1 wherein the diffusion imaging input data is acquired using any one or combination of magnetic resonance diffusion weighted imaging techniques such as diffusion tensor imaging, q-ball, and HARDI; and interferometric approaches including optical coherence tomography, and algorithmic segmentation.

10. The method according to claim 1 wherein the cerebrospinal tissue model of the patient's spinal cord includes further constituents, said further constituents including any one or combination of physical or biomechanical properties of any one or combination of spinal meninges, cerebral spinal fluid, vasculature, tumor, bone including vertebrae, intervertebral fibrocartilage, muscle, tendon, cartilage, or ligament.

11. The method according to claim 3 wherein the boundaries between tissue types includes boundaries between any combination of cerebral spinal fluid, meninges tumor, bone including vertebrae, intervertebral fibrocartilage, vasculature, muscle, tendon, cartilage, and ligament.

12. The method according to claim 11 wherein the fluid representations include cerebral spinal fluid, blood, and edema.

13. The method according to claim 1 wherein the diffusion imaging input data is acquired using any one or combination of magnetic resonance diffusion weighted imaging techniques such as diffusion tensor imaging, q-ball, and HARDI; and interferometric approaches including optical coherence tomography, and algorithmic segmentation.

14. A method of modelling effect of an influence on tissue using the evolvable cerebrospinal tissue model according to claim 1, comprising the steps of;
receiving at least one set of input data of at least one influence to which the diffusion imaging tissue is to be subjected;
preprocessing the at least one set of input data and extracting therefrom parameters of said influence;
representing the parameters of said influence in a preselected format; and
producing at least one influence model from the represented parameters of the influence; and
interacting the influence model with the cerebrospinal tissue model and updating the cerebrospinal tissue model after the interaction of the influence with the oriented diffusion fiber tract tissue map showing a transformation of the cerebrospinal tissue model due to the influence, the updated cerebrospinal tissue model forming an output.

15. The method according to claim 14, including using the updated cerebrospinal tissue model, and updated input data of the cerebrospinal tissue of the patient in the step of preprocessing the input data and extracting therefrom updated directional information of the at least one component of the diffusion imaging tissue, and including using the updated diffusion imaging tissue model, and updated input data of said at least one influence in the step of preprocessing the at least one set of input data and extracting therefrom updated parameters of said influence.

16. The method according to claim 14, wherein the step of interacting the influence model with the cerebrospinal tissue model includes iteratively interacting the influence model with the tissue model over a period of time, and including updating the diffusion imaging tissue model at selected times during said period of time.

17. The method according to claim 14 including visually displaying the updated cerebrospinal tissue model and/or storing the updated cerebrospinal tissue model.

18. The method according to claim 14, wherein the influence is a surgical instrument inserted into the tissue, and wherein the influence model includes at least dimensions and a shape of the instrument penetrating the cerebrospinal tissue, and wherein the method of modelling the effect of an influence includes an iterative process which includes movement of the instrument a given distance in a given period of time, with the output showing an amount of cerebrospinal tissue deformation at a selected time.

19. A system for producing an evolvable cerebrospinal tissue model of a patient, comprising:
a) a storage device computer readable storage medium configured to receive and store therein pre-operative and intra-operative input data of diffusion imaging tissue of a patient;
b) a computer processor and associated user interface in communication with said storage device computer readable storage medium, said computer processor being programmed with instructions for:
receiving at least one set of diffusion imaging input data of cerebrospinal tissue of a patient, said at least one set of input data containing at least directional information with respect to diffusion fiber tracts;
representing the directional information of the diffusion fiber tracts in a preselected format and producing therefrom an oriented diffusion fiber tract tissue map which reflects a directionality of the diffusion fiber tracts;
producing a cerebrospinal tissue model in which at least one constituent of the cerebrospinal tissue model uses the oriented diffusion fiber tract tissue map such that the cerebrospinal tissue model reflects the directionality of diffusion fiber tracts so that when the tissue model is subjected to an influence any evolution of the cerebrospinal tissue model over time incorporates the directionality of the diffusion fiber tracts; and wherein at least one additional constituent of the cerebrospinal tissue model uses the oriented diffusion fiber tract tissue map such that the cerebrospinal tissue model represents any one of the elasticity properties of the one or more tissue components, tensile properties of one or more tissue components or pressure properties of one or more tissue components as a geometric model;

storing said cerebrospinal tissue model in said storage device computer readable storage medium; and c) a visual display for displaying the cerebrospinal tissue model.

20. The method according to claim 1 wherein the input data contains fiber tract connectivity information from which fiber connectivity is derivable therefrom, and wherein another constituent of the cerebrospinal tissue model is the fiber connectivity.

\* \* \* \* \*